(12) United States Patent
Himmelsbach

(10) Patent No.: US 6,191,337 B1
(45) Date of Patent: Feb. 20, 2001

(54) SELF-ADHESIVE READY-MADE BANDAGE FOR IMMOBILIZING THE WRIST

(75) Inventor: Peter Himmelsbach, Buxtehude (DE)

(73) Assignee: Beiersdorf AG, Hamburg (DE)

( * ) Notice: Under 35 U.S.C. 154(b), the term of this patent shall be extended for 0 days.

(21) Appl. No.: 09/341,484

(22) PCT Filed: Jan. 17, 1998

(86) PCT No.: PCT/EP98/00250

§ 371 Date: Oct. 1, 1999

§ 102(e) Date: Oct. 1, 1999

(87) PCT Pub. No.: WO98/32404

PCT Pub. Date: Jul. 30, 1998

(30) Foreign Application Priority Data

Jan. 23, 1997 (DE) .............................................. 197 02 300

(51) Int. Cl.⁷ .................................................. A61F 13/00
(52) U.S. Cl. ................................................. 602/54; 602/41
(58) Field of Search ................. 602/54, 4, 304, 602/41

(56) References Cited

U.S. PATENT DOCUMENTS

| | | |
|---|---|---|
| 1,790,381 | 1/1931 | Keller . |
| 2,484,130 | 10/1949 | Thibault ............................ 128/166.5 |
| 2,875,758 | 3/1959 | Fuzak et al. ......................... 128/157 |
| 3,989,041 | 11/1976 | Davies ................................ 128/166 |
| 4,345,590 | 8/1982 | Nakajima ............................ 128/166 |

FOREIGN PATENT DOCUMENTS 2307518   11/1976   (FR) ............................... A61F/13/04

*Primary Examiner*—Michael A. Brown
*Assistant Examiner*—Lalita M. Hamilton
(74) *Attorney, Agent, or Firm*—Norris McLaughlin & Marcus

(57) ABSTRACT

Ready-made bandage with a self-adhesive coating on at least one side, for immobilizing the wrist, characterized in that at least three short reins (41, 43, 45) are arranged on one long side of an oblong strip (1), a second strip (2) is arranged on the opposite long side and encloses an angle of between 10° and 150° with the oblong strip (1), and a third strip (3) is arranged on one of the long sides of the second strip (2) and encloses an angle of between 30° and 150° with the second strip (2).

10 Claims, 1 Drawing Sheet

SELF-ADHESIVE READY-MADE BANDAGE FOR IMMOBILIZING THE WRIST

Figure 1:
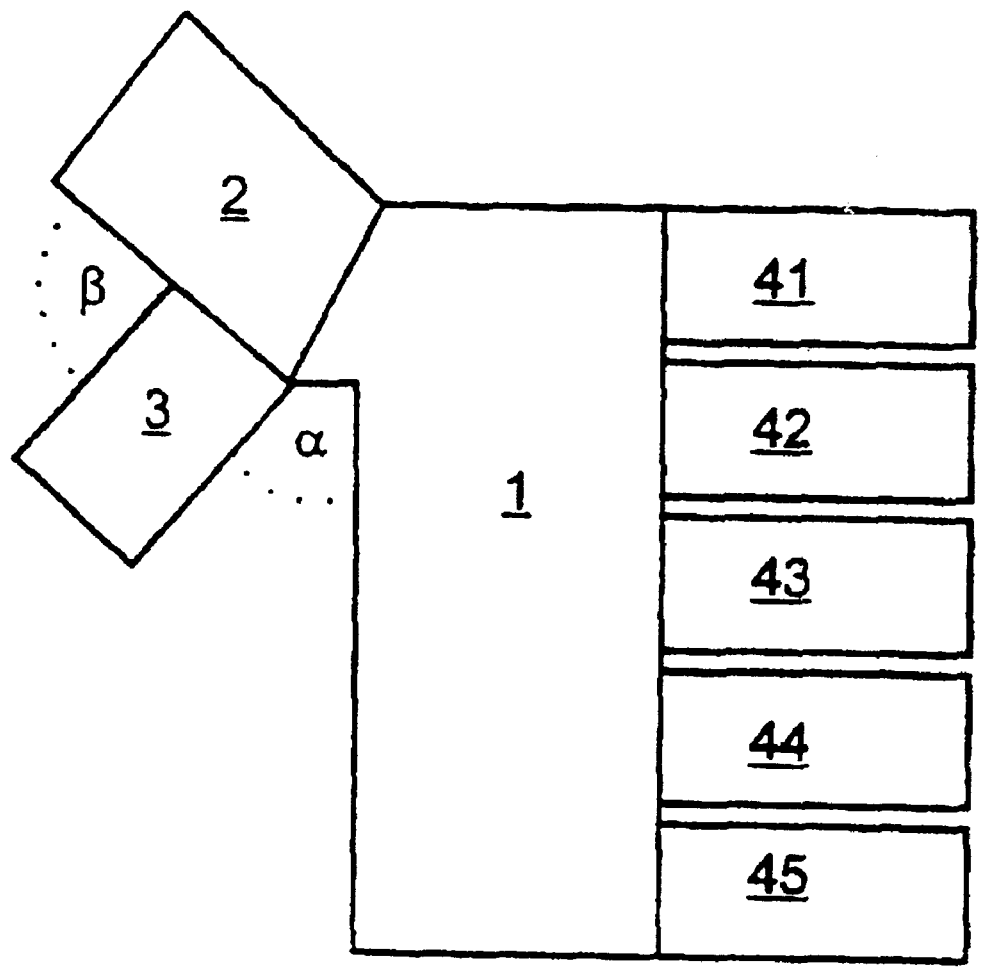

The invention relates to a ready-made bandage with a self-adhesive coating on one side, for immobilizing the wrist.

The functional dressing technique called taping is a treatment method for prevention and therapy of injuries, diseases and lesions of the locomotor apparatus. The aim of taping is to purposefully simulate the capsular ligament structures and in so doing to achieve selective support and stabilizing.

The actual tape dressing is applied in strips made up of preferably non-elastic self-adhesive tapes, so-called reins, or in conjunction with low-stretch elastic self-adhesive tapes. It protects, supports and relieves vulnerable, injured or damaged parts of a functional unit. It permits selective loading within the pain-free area of movement, but prevents extreme or painful movements.

However, the application of such dressings requires expert skill and experience and for this reason cannot generally be done by lay persons with no taping experience.

As regards the wrist, which is often exposed to very considerable mechanical stress, especially when performing sporting activities, which stress can lead to distortions and contusions, but also to straining of the ligaments in the wrist, the expert nevertheless requires a ready-made bandage which is of a simple construction and at the same time can be applied without problems, and which, especially in the case of minor injuries, has a positive influence on the healing process.

However, such a ready-made bandage should also be able to be applied by the lay person, affording the latter an economic and less time-intensive aid by means of the ready-made bandage.

The object of the invention was therefore to make available a ready-made bandage which, because of its construction, its material and its properties, is suitable for supporting the healing process in injuries of the wrist, and which in addition can be easily applied by the user.

This object is achieved by means of a ready-made bandage according to claim 1.

Accordingly, the ready-made bandage with a self-adhesive coating on at least one side, for immobilizing the wrist, is comprised of an oblong strip with at least three short reins arranged on one long side, and a second strip arranged on the opposite long side and enclosing an angle of between 10° and 150° with the oblong strip.

Moreover, a third strip is arranged on one of the long sides of the second strip and encloses an angle of between 30° and 150° with the second strip.

The short reins are preferably arranged at an angle of 90° to the oblong strip, it having proven particularly advantageous for the reins to be five in number.

In a further preferred embodiment, the oblong strip is about 12 cm to 30 cm long and 2 cm to 7 cm wide, the second strip is about 5 to 15 cm long and 2 to 6 cm wide, the third strip is about 4 to 12 cm long and 2 cm to 6 cm wide, and the reins are about 2 to 10 cm long and 2 cm to 6 cm wide.

The dimensions of the ready-made bandage are of course adapted to the size of the hand on which the ready-made bandage is being applied. For the average adult hand, the individual parts of the ready-made bandage have the following sizes:

The oblong strip is 18 cm long and 4 cm wide.
The second strip is 10 cm long and 4 cm wide.
The third strip is 8 cm long and 4 cm wide.
The reins are 6 cm long and 4 cm wide.

All the strips and reins can additionally also have rounded corners in order to reduce the risk of unintentional detachment of the adhered ready-made bandage.

It has proven particularly advantageous for cuttings or recesses to be present at the points where the oblong strip, the second strip, the third strip and/or the reins meet. These cuttings prevent the ready-made bandage from tearing at the points which have the highest loading, particularly during application. Alternatively, the recesses increase the flexibility of the ready-made bandage, so that alternatively application is made easier.

Again preferably, the self-adhesive ready-made bandage according to the invention is comprised of a non-elastic woven fabric or knitted fabric. Elastic or plastic components in the longitudinal direction or transverse direction of the support material can sometimes also advantageously influence user comfort. Furthermore, nonwovens or foams or paper can also be used if these have sufficient strength.

The support material can preferably be cotton and can additionally have a maximum tensile force of not less than 50 N/cm and a maximum tensile force extension of less than 20%.

On the side applied to the skin, the ready-made bandage is coated with one of the known good self-adhesive compositions based on rubber (preferably a zinc rubber composition) or synthetic polymers.

The self-adhesive composition can include solvent, dispersion/emulsion systems, but 100% self-adhesive composition systems can also be used. The compositions advantageously have other properties such as good skin compatibility or permeability to air and water vapour.

The self-adhesive composition is applied at about 100 g/m$^2$.

Prior to the bandage being used, the adhesive layer is covered with an anti-adhesive sheet material, for example siliconized paper, which can additionally be perforated for better use, or a foil of plastic.

The material can in this case be divided up into a plurality of sections in order to facilitate application of the ready-made bandage through successive detachment of the individual sections.

The self-adhesive ready-made bandage can be used universally for immobilizing the wrist.

The blank of the ready-made bandage naturally depends on which hand the ready-made bandage is intended for. Accordingly, there are two mirror-symmetrical embodiments of the ready-made bandage according to the invention.

The ready-made bandage can also be applied on the palmar or the dorsal surface of the hand, so that the blank has to be made separately depending on the application.

A particularly advantageous embodiment of the ready-made bandage according to the invention, and its use, are explained in greater detail with reference to the figure described hereinbelow.

FIG. 1 shows the bandage in its preferred embodiment. The ready-made bandage is here made up of several sections. The central section is formed by an oblong strip (1). A total of five short and rectangularly shaped reins (41, 42, 43, 44, 45) adjoin one of the long sides of the oblong strip (1) at right angles.

On the opposite long side of the oblong strip (1), and specifically at the edge to the transverse side, the oblong strip (1) widens in the form of a right-angled triangle. The second strip (2) adjoins the hypotenuse of the said triangle, and this second strip (2) likewise has an approximately rectangular shape.

Moreover, a third rectangularly shaped strip (3) is formed on the second strip (2) in such a way that the oblong strip (1), the second strip (2) and the third strip (3) touch at one point.

The angle $\alpha$ between the third strip (3) and the oblong strip (1) is 45°, and the angle $\beta$ between the second strip (2) and the third strip (3) is 90°.

To apply the bandage, the oblong strip (1) is applied on the palmar surface at the attachment of the middle finger, so that the oblong strip (1) runs over the wrist as far as the lower arm. The second strip (2) is then attached so that it extends from the metacarpal area, between thumb and index finger, to the dorsal surface of the hand. The third strip (3) runs over the ball of the thumb to the dorsal surface of the hand.

Finally, the five reins (41, 42, 43, 44, 45) are guided in a circle round the hand, the wrist and the forearm.

In this way, the mobility of the wrist is restricted almost to complete immobilization. Still greater restriction can be achieved by means of additional reins being attached round the hand, the wrist and the forearm or by means of further anchoring strips reinforcing the dressing.

What is claimed is:

1. Ready-made wrist bandage with a self-adhesive coating on at least one side, for immobilizing the wrist wherein at least three short reins are arranged on one long side of an oblong strip, a second strip is arranged on the opposite long side and encloses an angle of between 10° and 150° with the oblong strip, and a third strip is arranged on one of the long sides of the second strip and encloses and angle of between 30° and 150° with the second strip.

2. Self-adhesive ready-made wrist bandage according to claim 1 wherein the reins are arranged at an angle of 90° to the oblong strip.

3. Self-adhesive ready-made wrist bandage according to claim 1, wherein five reins are arranged on said one side of said oblong strip.

4. Self-adhesive ready-made wrist bandage according to claim 3, wherein the oblong strip is about 12 to 30 cm long and 2 cm to 7 cm wide, the second strip is about 5 cm to 15 cm long and 2 cm to 6 cm wide, and the reins are about 2 to 10 cm long and 2 cm to 6 cm wide.

5. Self-adhesive ready-made wrist bandage according to claim 4, wherein the reins have identical dimensions.

6. Self-adhesive ready-made wrist bandage according to claim 1, wherein cuttings are present at the points where the oblong strip and the second strip meet; where the third strip and the second strip meet; and where the reins and the oblong strip meet.

7. Self-adhesive ready-made wrist bandage according to claim 1, wherein the ready-made bandage is comprised of a non-elastic support material selected from the group consisting of nonwovens, papers, foams, woven fabrics and knitted fabrics.

8. Self-adhesive ready-made wrist bandage according to claim 7, wherein said bandage is comprised of a nonwoven fabric and the nonwoven fabric is cotton and has a maximum tensile force of not less than 50 N/cm and a maximum tensile force extension of less than 20%.

9. Self-adhesive ready-made wrist bandage according to claim 1, wherein the ready-made bandage is covered, on its self-adhesive side, with anti-adhesive material.

10. A method for immobilizing a wrist of a human hand, which comprises applying a wrist bandage of claim 1 to said wrist.

* * * * *